(12) United States Patent
Watanabe et al.

(10) Patent No.: US 9,707,310 B2
(45) Date of Patent: Jul. 18, 2017

(54) AIR CLEANING DEVICE, AIR CLEANING METHOD USING THE AIR CLEANING DEVICE, AND AIR CLEANING SYSTEM

(71) Applicant: APS Japan Co., Ltd., Osaka-shi (JP)

(72) Inventors: Teruo Watanabe, Osaka (JP); Hidemitsu Watanabe, Osaka (JP); Hiroyuki Watanabe, Osaka (JP); Takafumi Watanabe, Osaka (JP)

(73) Assignee: APS JAPAN CO., LTD., Osaka-shi (JP)

( * ) Notice: Subject to any disclaimer, the term of this patent is extended or adjusted under 35 U.S.C. 154(b) by 0 days.

(21) Appl. No.: 14/834,691

(22) Filed: Aug. 25, 2015

(65) Prior Publication Data

US 2016/0051719 A1  Feb. 25, 2016

(30) Foreign Application Priority Data

Aug. 25, 2014 (JP) ................. 2014-170711

(51) Int. Cl.
*A61L 9/00* (2006.01)
*A61L 9/20* (2006.01)
*A61L 9/22* (2006.01)

(52) U.S. Cl.
CPC .................... *A61L 9/205* (2013.01)

(58) Field of Classification Search
CPC ....................................... A61L 9/205
USPC ........................................ 422/121
See application file for complete search history.

(56) References Cited

U.S. PATENT DOCUMENTS

| | | | |
|---|---|---|---|
| 2007/0159825 A1* | 7/2007 | Ham | A61L 9/205 362/260 |
| 2012/0275960 A1* | 11/2012 | Seck | A62B 15/00 422/121 |
| 2013/0094204 A1* | 4/2013 | Budai | F21V 33/00 362/230 |
| 2015/0273101 A1* | 10/2015 | Sung | A61L 9/22 422/121 |

FOREIGN PATENT DOCUMENTS

JP  2006-034986 A  2/2006

\* cited by examiner

*Primary Examiner* — Kevin Joyner
*Assistant Examiner* — Holly Mull
(74) *Attorney, Agent, or Firm* — Kratz, Quintos & Hanson, LLP (57) ABSTRACT

To provide an illuminating device-cum-air cleaning device that solves a heat problem and allows efficient operation of an air cleaning means.
Air inlets/outlets 3A and 3B are provided in a wall surface of a housing 10 to which an illumination light source 2 is attached. A fan 4 is provided in the housing 10 to generate a forced air flow inside and outside the housing 10 through the air inlets/outlets 3A and 3B and discharge heat from the illumination light source 2 by the forced air flow to the outside of the housing 10. In the middle of a flow path for the forced air flow a within the housing 10, a photocatalyst 50 facing the flow path and a UV light source 51 irradiating the photocatalyst 50 with light including ultraviolet rays are provided as air cleaning means 5.

11 Claims, 11 Drawing Sheets

AIR CLEANING DEVICE, AIR CLEANING METHOD USING THE AIR CLEANING DEVICE, AND AIR CLEANING SYSTEM

TECHNICAL FIELD

The present invention relates to an air cleaning device that includes an illumination light source and an air cleaning means and performs the function of an illuminating device.

BACKGROUND ART

There has been conventionally proposed an air cleaning device of this type composed of a light bulb-shaped casing that has at one end a base part attached to a power feeding part and connected to a commercial power source and has at the other end a blowing port and a light bulb; and an ozone generator that is housed in the casing such that the blowing port and a first electrode are opposed to each other to generate and release negative ions and ozone through the blowing port (refer to Patent Document 1).

However, the conventionally proposed illuminating device-cum-air cleaning device has a heat problem, that is, a problem that heat generated by both of the illumination light source and the air cleaning means persists within the casing, and a problem that the air cleaning means cannot operate efficiently within a limited space adjacent to the illumination light source.

CITATION LIST

Patent Literature

Patent Document 1: JP-A No. 2006-034986

SUMMARY OF INVENTION

Technical Problem

In view of the foregoing circumstances, an object of the present invention is to provide an illuminating device-cum-air cleaning device that solves the heat problem and allows efficient operation of the air cleaning means.

To solve the foregoing problems, the present invention is an air cleaning device in which air inlets/outlets are provided in a housing to which an illumination light source is attached, a fan is provided in the housing to generate a forced air flow inside and outside the housing through the air inlets/outlets and discharge heat from the illumination light source by the forced air flow to the outside of the housing, and an air cleaning means is provided in the middle of a flow path for the forced air flow within the housing.

It is preferred that the air cleaning device has a light source support base made from a highly thermal-conductive member with an outer surface to which the illumination light source is fixed, and an inner surface of the light source support base opposite to the illumination light source constitutes an inner wall surface of the flow path.

It is preferred that a heat sink member made from a highly thermal-conductive member is protruded from the inner surface of the light source support base such that the heat from the light source support base is discharged via the heat sink member to the forced air flow passing through the flow path.

It is preferred that the illumination light source is composed of an illumination LED.

It is preferred that the air cleaning means is a photocatalyst facing the flow path and an UV light source irradiating the photocatalyst with light including ultraviolet rays.

It is particularly preferred that the UV light source is fixed to the inner surface of the light source support base or the heat sink member.

It is preferred that the UV light source is composed of an ultraviolet LED.

It is preferred that the air cleaning means is a means for generating ions or radical active species by discharge of a high voltage to be applied to electrodes.

It is preferred that the air cleaning device is a light bulb type with a base to which power is supplied from the outside.

The present invention provides an air cleaning method including: disposing one or more air cleaning devices described above on an inner surface of a space divided from others and intended as a humans' or animals' activity space or as a storage space for objects; illuminating the inner space by the air cleaning device; taking into the housing the air from the inner space as the forced air flow; and cleaning the air by the air cleaning means in the middle of the flow path and emitting the same to the outside of the housing, thereby to clean the air in the inner space.

It is preferred that the air cleaning device is a light bulb type with a base to which power is supplied from the outside, the air cleaning device is detachably attached through the base to the inner surface of the storage space, and a socket is provided to supply power to the attached air cleaning device, and the illumination light source, the fan, and the air cleaning means in the air cleaning device, are operated by the power supply.

The present invention also provides an air cleaning system wherein one or more air cleaning devices described above are disposed on an inner surface of a space divided from others and intended as a humans' or animals' activity space or as a storage space for objects, the inner space is illuminated by the air cleaning device; the air in the inner space is taken into the housing as the forced air flow, and the air is cleaned by the air cleaning means in the middle of the flow path and is emitted to the outside of the housing, thereby to clean the air in the inner space.

It is also preferred in this system that the air cleaning device is a light bulb type with a base to which power is supplied from the outside, the air cleaning device is detachably attached through the base to the inner surface of the storage space, and a socket is provided to supply power to the attached air cleaning device such that the illumination light source, the fan, and the air cleaning means in the air cleaning device, are operated by the power supply.

Advantageous Effects of Invention

In the thus configured air cleaning device according to the present invention, the air inlets/outlets are provided in the housing to which the illumination light source is attached, a fan is provided in the housing to generate a forced air flow inside and outside the housing through the air inlets/outlets and discharge heat from the illumination light source by the forced air flow to the outside of the housing, and the air cleaning means is provided in the middle of the flow path for the forced air flow in the housing. Accordingly, it is possible to discharge efficiently both the heat from the illumination light source and the heat from the air cleaning means by the forced air flow generated by the fan, and allow the illumination light source and the air cleaning means to be disposed in a compact and efficient manner. In addition, the air cleaning means cleans the air as the forced air flow taken by the fan from the air inlets/outlets into the housing and discharges forcibly the same to the outside from the air inlets/outlets. Accordingly, it is possible to allow the air cleaning means to operate and clean the air around the device in an efficient manner.

In addition, the air cleaning device has the light source support base made from a highly thermal-conductive member with the outer surface to which the illumination light source is fixed, and the inner surface of the light source support base opposite to the illumination light source constitutes the inner wall surface of the flow path. Accordingly, the heat generated by the illumination light source is transferred to the light source support base and is efficiently discharged by the forced air flow contacting the inner surface of the light source support base. As a result, it is possible to separately dispose the illumination light source and the air cleaning means with the light source support base therebetween, and efficiently transfer the heat from the illumination light source to the forced air flow passing through the air cleaning means through the light source support base.

The heat sink member made from a highly thermal-conductive member is protruded from the inner surface of the light source support base such that heat from the light source support base is discharged via the heat sink member to the forced air flow passing through the flow path. This allows the heat from the illumination light source to be discharged more efficiently to the forced air flow.

The illumination light source is made from an illumination LED, which allows power saving and increases power distribution to the air cleaning means to enhance the function of the air cleaning means. In addition, when the temperature of the LED rises to 90 degrees or more, the LED becomes reduced in light output and lifetime. However, the present invention allows efficient discharge of heat from the illumination LED by the forced air flow from the fan as described above, and thus prevents such a problem.

Provided as the air cleaning means are the photocatalyst facing the flow path and the UV light source irradiating the photocatalyst with light including ultraviolet rays. It is thus possible to clean by the action of the photocatalyst the air as the forced air flow taken into the housing, and then discharge the same to the outside, thereby realizing efficient cleaning of the air around the device. Although the UV light source is a light source prone to generate heat, the UV light source in the present invention is provided in the flow path for the forced air flow to allow the heat from the UV light source to be efficiently discharged in the same way as the heat from the illumination light source.

The UV light source is fixed to the inner surface of the light source support base or the heat sink member, and thus the heat generated by the UV light source can be efficiently discharged to the forced air flow through the light source support base and the heat sink member, in the same way as the heat generated by the illumination light source.

The UV light source is composed of an ultraviolet LED, and it is thus possible to achieve power saving and light amount increase, and discharge efficiently the heat from the ultraviolet LED by the forced air flow from the fan described above to prevent reduction in light power and lifetime.

Provided as the air cleaning means is the means for generating ions or radical active species by discharge of a high voltage to be applied to the electrodes. It is thus possible to clean the air as the forced air flow taken into the housing by the ions or radical active species, and then discharge the same to the outside, thereby realizing efficient cleaning of the air around the device.

The air cleaning device is a light bulb type with the base to which power is supplied from the outside, and thus can be easily attached to a ceiling in a room or the like in the same way as conventional light bulbs. The air cleaning device can be easily used as an illuminating device-cum-air cleaning device simply by attaching to the ceiling or the like, which makes it possible to add the air cleaning function by replacing the existing light bulb.

According to the air cleaning method or the air cleaning system wherein one or more air cleaning devices according to the present invention are disposed on the inner surface of the space divided from others and intended as a humans' or animals' activity space or as a storage space for objects, the inner space is illuminated by the air cleaning device; the air in the inner space is taken into the housing as the forced air flow; and the air is cleaned by the air cleaning means in the middle of the flow path and is emitted to the outside of the housing, thereby to clean the air in the inner space, it is possible to provide illumination required for humans' or animals' activities and allow efficient cleaning of the air in the activity space. Accordingly, it is possible to make the space healthy by decomposing air-pollution substances and harmful substances such as acetaldehyde and sterilizing airborne bacteria. It is also possible to provide illumination during working in the storage space for objects such as a food warehouse, for example, and contribute to preservation of food freshness by decomposing gases and germs from food and the like.

In addition, the air cleaning device is a light bulb type with the base to which power is supplied from the outside, the air cleaning device is detachably attached to the inner surface facing the storage space through the base, the socket is provided to supply power to the attached air cleaning device, and the illumination light source, the fan, and the air cleaning means in the air cleaning device are activated by the power supply. Accordingly, the air cleaning device can be easily attached to a ceiling in a room or the like in the same way as conventional light bulbs. The air cleaning device can be easily used as an illuminating device-cum-air cleaning device simply by attaching to the ceiling or the like, which makes it possible to add the air cleaning function by replacing the existing light bulb.

DESCRIPTION OF EMBODIMENTS

Embodiments of the present invention will be described below in detail with reference to the accompanying drawings. First, a first embodiment will be described with reference to FIGS. 1 and 2.

Figure 1:
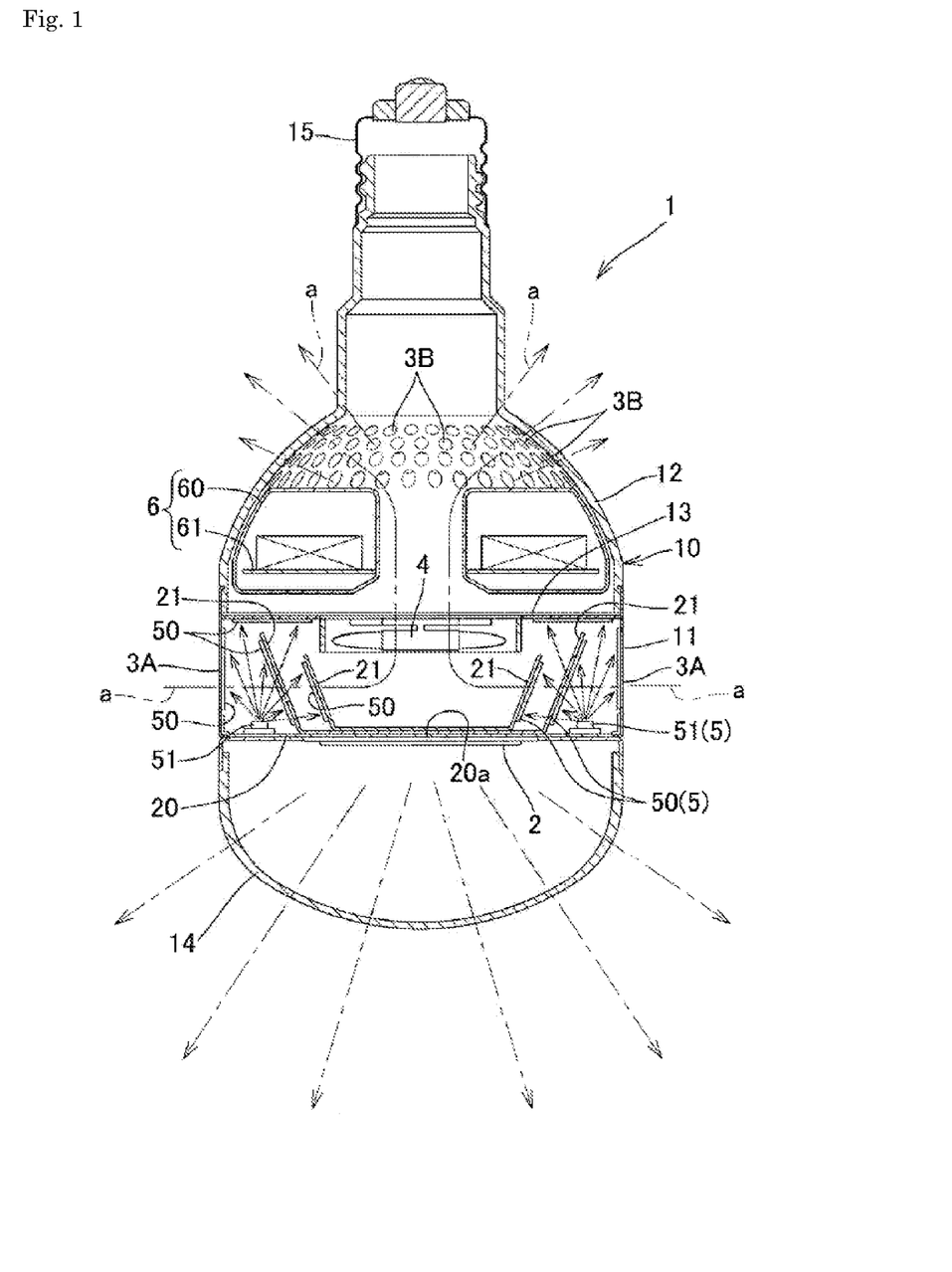
FIG. 1 is an illustrative cross-sectional view of an air cleaning device according to a first embodiment of the present invention.

In an air cleaning device 1 of the first embodiment, as illustrated in FIG. 1, air inlets/outlets 3A and 3B are provided in a wall surface of a housing 10 to which an illumination light source 2 is to be attached, a fan 4 is provided in the housing 10 to generate forced air flows (shown by arrows a in FIG. 1) inside and outside the housing 10 through the air inlets/outlets 3A and 3B and discharge heat generated by the illumination light source 2 to the outside of the housing 10, and a photocatalyst 50 facing flow paths for the forced air flows a in the housing 10 and a UV light source 51 emitting light including ultraviolet rays to the photocatalyst 50 are provided as air cleaning means 5 in the middle of the flow paths.

The first embodiment is configured on the basis of the illumination device described in JP-A No. 2013-175451 except for the configuration of the air cleaning means 5. The following description will be based on the basic configuration but the first embodiment is not limited to this configuration. In the air cleaning device 1, a lens body 14 covering the illumination light source 2 is provided at the leading end of the housing 10, and a base 15 to be connected to an external power source is provided at the base end of the housing 10. The size of the base may be any one of various sizes such as E26 and E39. In the illustrated example, the air cleaning device is formed in a light bulb shape, but the present invention is not limited to this. The air cleaning device may be an illuminating device-cum-air cleaning device of any other type such as a ceiling light as a ceiling-mounted illuminating device or a straight fluorescent type.

The illumination light source 2 may be an illumination LED module or any other conventional publicly-known light source for illuminating device such as a fluorescent lamp, a halogen lamp composed of filaments, high-intensity discharge lamps (high-pressure sodium lamp, metal halide lamp (multi-halogen lamp), mercury lamp, or the like). The lens body 14 may be any one of conventional publicly-known lens bodies. The illumination light source 2 is supported on the surface of the leading end of a light source support base 20 made from a highly thermal-conductive member of aluminum or the like, and is stored in almost sealed state between the light source support base 20 and the lens body 14.

The air inlets/outlets 3A and 3B are provided in the wall surface of the housing 10 at the base end side beyond the light source support base 20, and the fan 4 is provided in the inside of the housing 10 to generate the forced air flow a inside and outside the housing 10 through the air inlets/ outlets 3A and 3B. The surface of the light source support base 20 at the base end side (inner surface 20a opposite to the illumination light source 2) constitutes the inner wall of the flow paths for the forced air flows a. The UV light source 51 is fixed to the inner surface 20a and is configured to emit ultraviolet rays to the photocatalyst 50 described later.

The UV light source 51 is an ultraviolet LED module but is not limited to this and may be a conventional ultraviolet lamp or the like. However, the ultraviolet LED is longer in lifetime as compared to the conventional ultraviolet lamps that need to be replaced in about one year, and thus the ultraviolet LED is suited for use in the illuminating device-cum-air cleaning device in the present invention, in particular, the light bulb type. The heat generated by the illumination light source 2 and the UV light source 51 is efficiently discharged by the forced air flows a from the inner surface 20a of the light source support base 20 to the outside of the housing 10. That is, the structure with the fan 4 allows efficient heat discharge from both of the illumination light source 2 and the UV light source 51.

In the first embodiment, the UV light source 51 is fixed to the inner surface 20a of the light source support base 20, and the heat from the UV light source 51 is efficiently discharged to the forced air flows a through the light source support base 20. The position of the UV light source 51 is not limited to the foregoing one but the UV light source 51 may be provided at a heat sink member 21 or may be provided at any other appropriate position where the photocatalyst 50 can be efficiently irradiated. In addition, there is no particular limitation on the number of the UV light source 51.

The heat sink member 21 composed of highly thermal-conductive members of aluminum or the like is protruded on the inner surface 20a of the light source support base 20, and the heat from the illumination light source 2 and the UV light source 51 is efficiently discharged from the light source support base 20 and the heat sink member 21 to the forced air flows a passing through the flow paths. The heat sink member 21 is formed such that a plurality of plate-like fins is bent and integrated into two large and small similarly-shaped members at the outer peripheries of plate-like support parts and the two members are aligned at the center and axially attached at the support parts to each other.

The thus configured heat sink member 21 has flow paths through which the forced air flows pass between the plate-like fins to allow efficient discharge of the heat transferred to the plate-like fins. In addition, the heat sink member 21 also has flow paths between the plate-like fins of the two large and small members adjacent to each other in the radial direction, which constitutes the flow paths through which the forced air flows pass around all of the plate-like fins to achieve more efficient heat discharge. The layer of the photocatalyst 50 is formed by coating or the like on the surfaces of the plate-like fins to be irradiated with ultraviolet rays by the UV light source 51. This ensures the large surface area of the layer of the photocatalyst 50 that is subjected to the photocatalytic action, and allows the forced air flows a to efficiently contact the layer of the photocatalyst 50 to improve the air cleaning action.

The housing 10 is composed of a first case 11 with the leading end portion to which the light source support base 20 is connected and a second case 12 with the base end portion at which the base 15 is provided. The air inlets/outlets 3A and 3B are provided at the side wall portions of the first case 11 and the second case 12, respectively. The fan 4 is positioned in the housing 10 between the air inlets/outlets 3A of the first case 11 and the air inlets/outlets 3B of the second case 12. According to the rotation direction of the fan 4, the forced air flows are generated in the housing such that the air inlets/outlets 3A or 3B take in the outside air and the air inlets/outlets 3A or 3B release the air.

In this example, a centrally-opened support plate 13 composed of a highly thermal-conductive member of aluminum or the like is positioned near the boundary between the connected first case 11 and second case 12, and the fan 4 is fixed to the support plate 13 to close the opening. The surface of the support plate 13 at the leading end side constitutes the inner wall of the flow paths for the forced air flows a, and serves as a heat sink for the fan 4. The layer of the photocatalyst 50 is formed by coating or the like on the surface of the support plate 13 at the leading end side.

The first case 11 is composed of a highly thermal-conductive member of aluminum or the like, and also serves as a heat sink that discharges heat in the illumination light source 2 and the UV light source 51 transferred from the light source support base 20 to the forced air flows contacting the case inner surface and the outside air contacting the case outer surface. The first case 11 has a plurality of axially extending slit-like penetrating grooves as the air inlets/outlets 3A in the side wall portion at predetermined intervals in a circumferential direction. The layer of the photocatalyst 50 is formed by coating or the like on the inner surface of the side wall portion and has the function of cleaning the forced air flows a through the air inlets/outlets 3A by the photocatalytic action of irradiation of the UV light source 51.

A power supply circuit part 6 is positioned between the air inlets/outlets 3A and 3B in the housing 10. The heat generated by the power supply circuit part 6 is also discharged by the forced air flows from the fan 4 to the outside of the housing 10. In this case, the power supply circuit part 6 is formed such that a centrally-opened annular plate-like circuit substrate 61 is included in a centrally-opened annular hollow resin case 60.

The second case 12 is an insulating synthetic resin molded part that includes an almost dome-shaped leading end-side case portion continuously reduced in diameter from the leading end opening to the base end side, and an almost cylindrical base end-side case portion that is continuously extended from the leading end-side case portion to the base end side, is reduced in diameter with one or more steps in the middle, and has a male screw portion for attachment of the base 15 on the outer periphery of the base end portion. The second case 12 has a plurality of penetrating holes as the air inlets/outlets 3B to penetrate through the wall surface of the second case 12 closer to the base end beyond the position where the power supply circuit part 6 is disposed. Although the wiring structure is not illustrated in the drawing, a lead wire for power input is provided from the power supply circuit part 6 to the base 15, and lead wires for power supply are provided from the power supply circuit part 6 to the illumination light source 2, the fan 4, and the UV light source 51.

In this example, the air cleaning means 5 composed of the UV light source 51 and the photocatalyst 50 is provided in the space closer to the illumination light source 2 than the fan 4, specifically, in the inner side of the first case 11. However, the position of the air cleaning means 5 is not limited to this and the air cleaning means 5 may be provided in the second case 12 or may be provided in both. In this example, the side closer to the illumination light source 2 than the fan 4 is designated as upstream side of the forced air flows a and the air cleaning means 5 is provided at the upstream side. However, the direction of the forced air flows a may be reversed, or the air cleaning means 5 may be provided in the inner space at the downstream side, not the upstream side, or may be provided in both as described above.

In this example described above, the layer of the photocatalyst 50 is used as a coating or the like. Alternatively, the separate sheet-like layer of the photocatalyst 50 may be attached to the applicable surfaces, or separate members with the layer of the photocatalyst 50 on the surface may be attached to the positions irradiated with ultraviolet rays by the UV light sources in the middle of the flow paths for the forced air flows. Otherwise, filter-like members letting through the forced air flows may hold the photocatalyst 50 and attach to the positions irradiated with ultraviolet rays by the UV light sources in the middle of the flow paths for the forced air flows. Further alternatively, the heat sink member 21 may be formed as a perforated plate letting the air through and be coated with the photocatalyst 50.

The photocatalyst 50 may be conventional publicly-known titanium oxide, zinc oxide, zirconium oxide, or the like. The UV light source 51 may be an ultraviolet LED with a wavelength of 200 to 420 nm. The wavelength may be selected as appropriate according to the kind of the photocatalyst. For example, in the case of using titanium oxide, an ultraviolet LED with a wavelength of 365 to 385 nm is preferably used.

Figure 2:
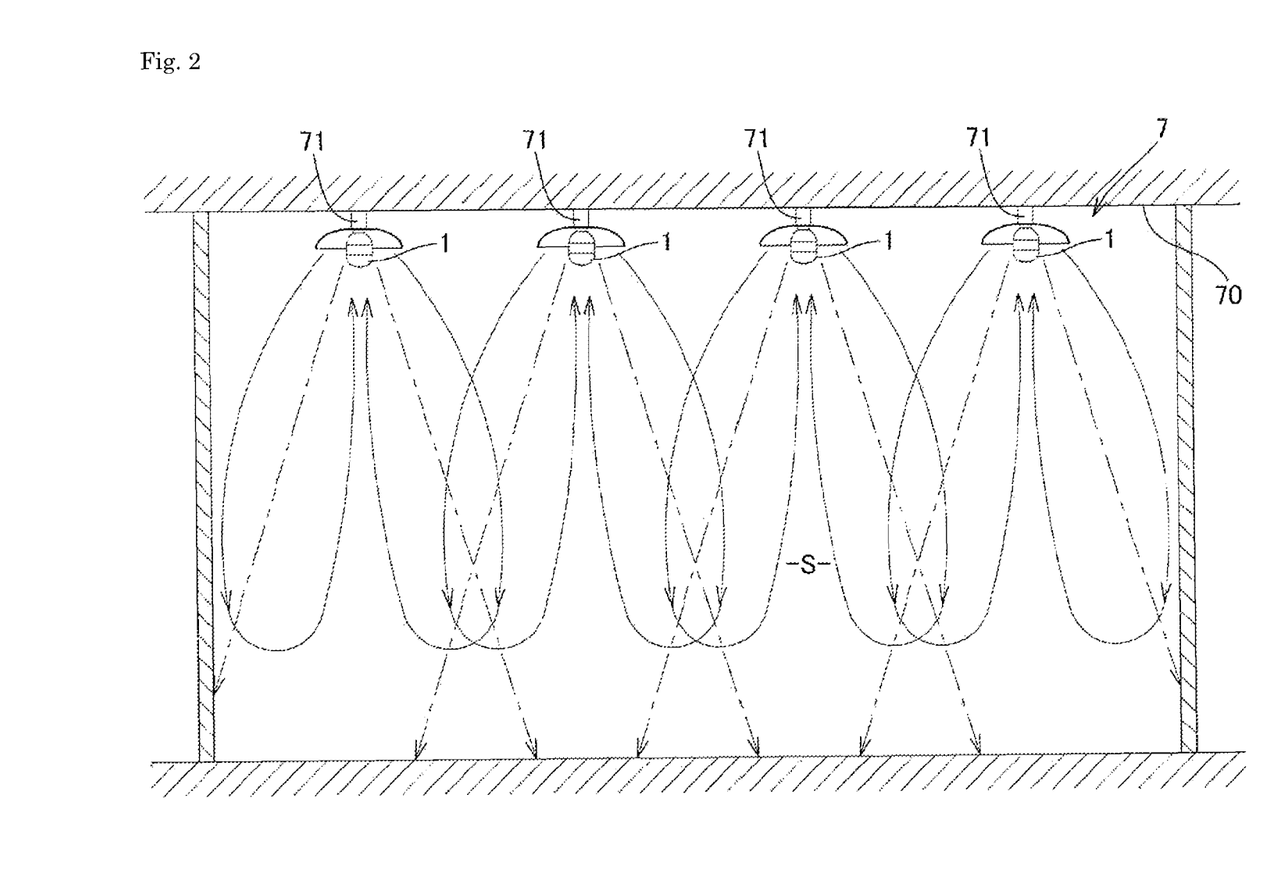
FIG. 2 is an illustrative view of an air cleaning system using the air cleaning devices.

FIG. 2 illustrates one example of an air cleaning system 7 in an inner space S divided from others that constitutes a humans' or animals' activity space or a storage space for objects. A plurality of air cleaning devices 1 is disposed on an inner surface of the inner space S, in this example, on a ceiling 70, such that each of the air cleaning devices 1 illuminates the inner space S and takes in air from the inner space S as forced air flows into the housings of the air cleaning device 1, and the air cleaning means in the middle of the flow paths cleans the air and releases the same to the outside of the housings, thereby to clean the air in the inner space S.

According to the air cleaning system 7 as described above, the air cleaning devices can be used as general lighting devices in a personal residence or an office room as the space S and can make the space S healthy by decomposing air-pollution substances and harmful substances such as acetaldehyde and influenza viruses and sterilizing air-borne bacteria. In addition, according to the air cleaning system 7, the air cleaning devices can be used as general illuminating devices in a food storage room (refrigerating room, agricultural cooperative warehouse, air cargo facility (airfreight), or the like) or store shelves as the space S, for example, and can contribute to preservation of food freshness by decomposing gases and germs from food and the like in the warehouse or the case. The space S may be any of other various spaces.

The air cleaning device 1 is a light bulb type with the base 15 and can be easily attached to the ceiling with the use of a conventional light bulb socket 71 on the ceiling. Accordingly, the air cleaning device 1 can be easily used an illuminating device-cum-air cleaning device, which makes it possible to add the air cleaning function by replacing the existing light bulb.

Figure 3:
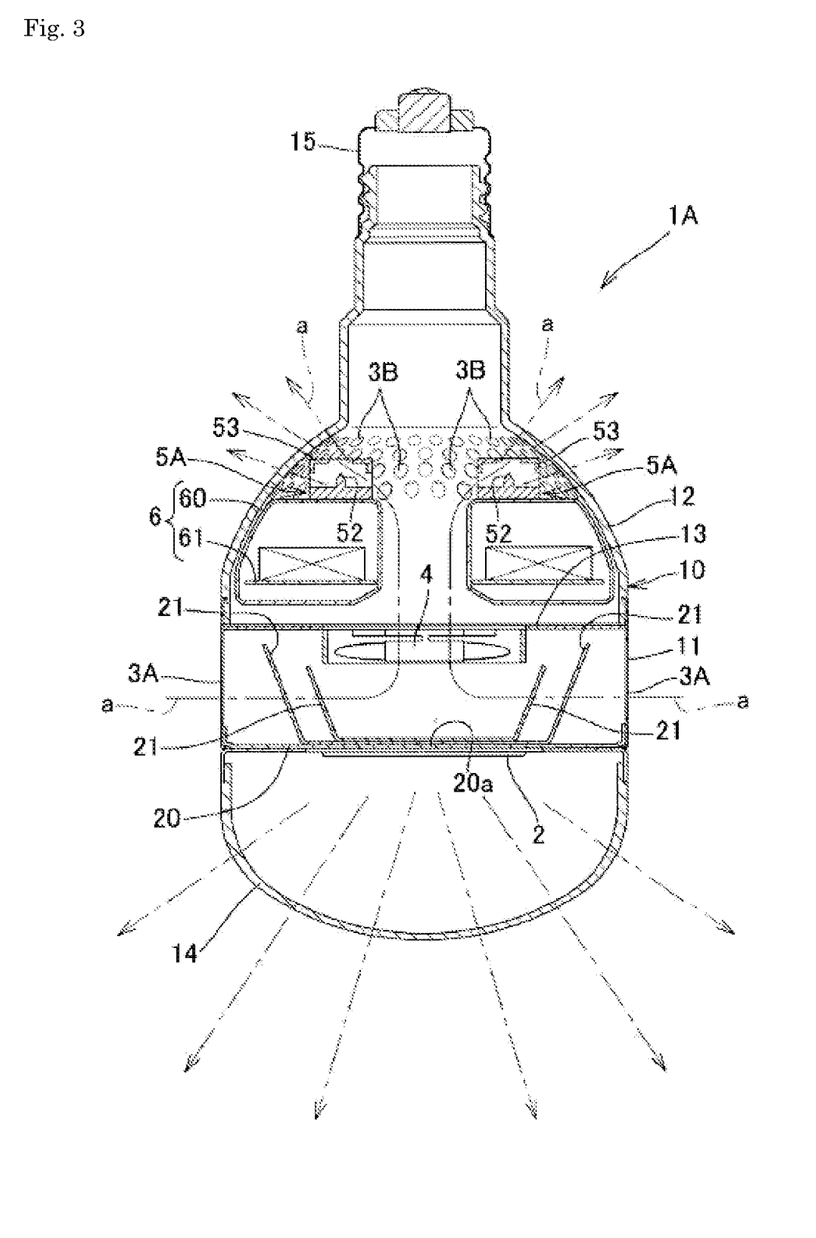
FIG. 3 is an illustrative cross-sectional view of an air cleaning device according to a second embodiment of the present invention.

Next, a second embodiment will be described with reference to FIG. 3.

An air cleaning device 1A in this embodiment is provided with a means for generating ions or radical active species by discharge of a high voltage to be applied between electrodes 52 and 53 as air cleaning means 5A.

The air cleaning means 5A may be a means for applying a direct-current high voltage between the electrodes and generating negative ions by corona discharge as disclosed in JP-A No. 2006-034986 or JP-A No. 2007-305321, for example, or may be a means for applying an alternating-current voltage between electrodes opposed to each other with a dielectric body therebetween and generating positive and negative ions as described in JP-A No. 2002-095731, or may be a means for cooling electrodes by a Peltier cooler and applying a high voltage to condensed water to generate OH radicals covered by the water (for example, a "nanoe" device produced by Panasonic Corporation).

In particular, in the case of using the means for generating the OH radicals covered by the water, the surrounding environmental temperature needs to be 5 to 40° C. because the means is structured to condense water on the electrodes by cooling. In contrast, the air cleaning device 1A in the present invention serves also as an illuminating device and increases the temperature around the device by heat from the illumination LED. Accordingly, even in an unusable environment such as the inner space of a refrigerator, for example, the temperature of the atmosphere around the device becomes partially higher and then the atmosphere takes on moisture to allow the means to generate the OH radicals covered by the water.

The air cleaning device 1A in this embodiment can make the space healthy by decomposing air-pollution substances and harmful substances such as acetaldehyde and sterilizing airborne bacteria, and can contribute to preservation of food freshness by decomposing gases and germs from food and the like, in the same way as the air cleaning device in the first embodiment. Accordingly, the air cleaning device 1A can be used in the air cleaning system 7 as in the first embodiment. The components of the air cleaning device 1A except for the air cleaning means 5A are basically the same as those in the first embodiment, and the same components will be given the same reference signs and descriptions thereof will be omitted. As a matter of course, the air cleaning means 5 in the first embodiment (the photocatalyst 50 and the UV light source 51) and the air cleaning means 5A in the second embodiment (the means for generating ions or radical active species) may be combined in one device.

Figure 4:
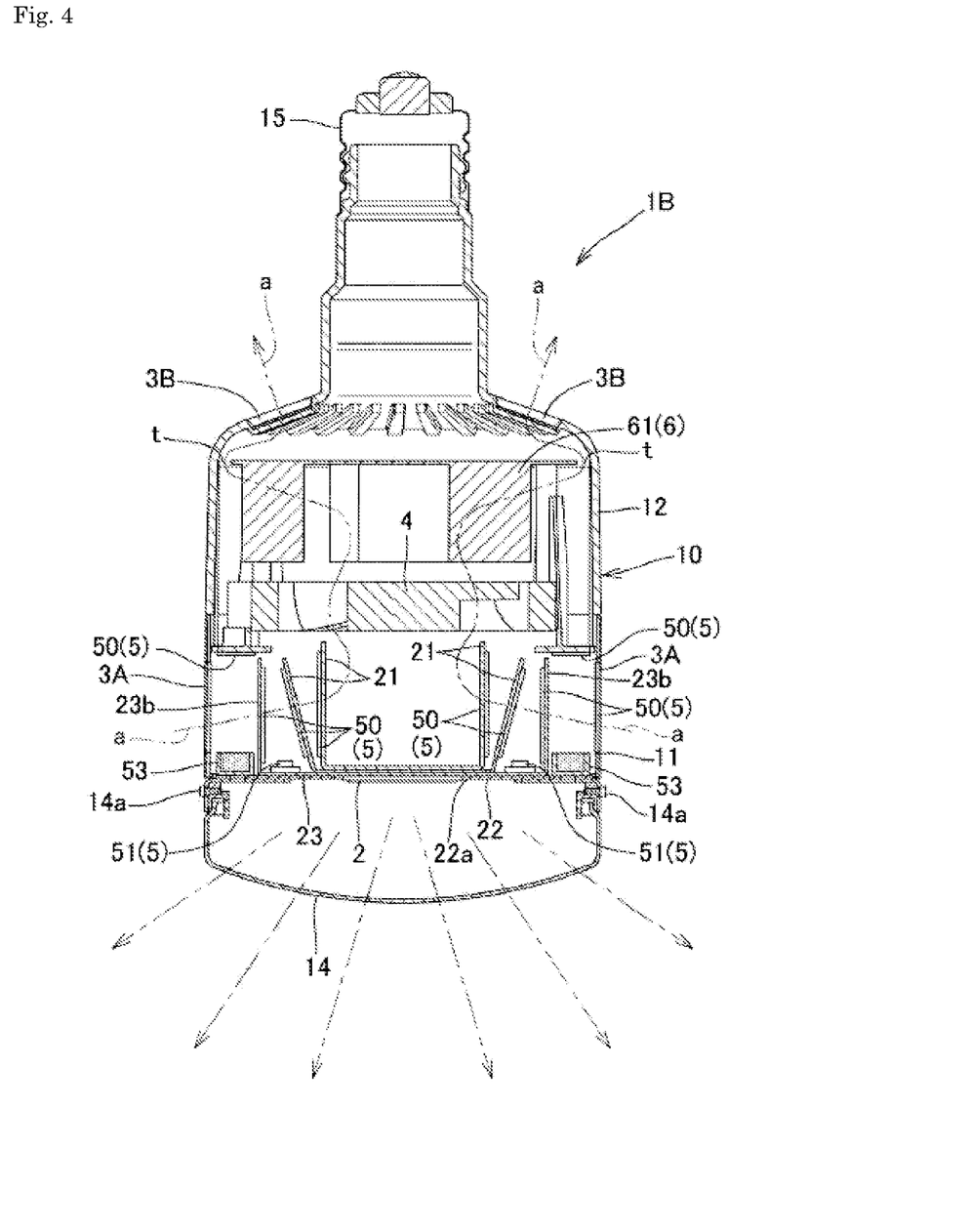
FIG. 4 is an illustrative cross-sectional view of an air cleaning device according to a third embodiment of the present invention.

Next, a third embodiment will be described with reference to FIG. 4.

In an air cleaning device 1B of this embodiment, the light source support base 20 is composed of a centrally-bored plate-like base plate 22 and a support plate 23 overlapped and fixed to the base end-side surface of the base plate 22. The base plate 22 and the support plate 23 are both made from a highly thermal-conductive member of aluminum or the like. The illumination light source 2 is fixed to the leading end-side surface of the support plate 23 exposed to the opening 22a of the bored base plate 22.

The peripheral edge part of the support plate 23 is bent toward the base end side and is protruded in the flow paths for the forced air flows a in the same way as the heat sink member 21, so that heat from the illumination light source 2 can be efficiently released to the flow paths for the forced air flows a. The UV light source 51 as the air cleaning means 5 is also fixed to the base end-side surface of the support plate 23, so that heat from the UV light source 51 can also be efficiently released to the flow paths. The UV light source 51 may be fixed to another position.

In this embodiment, the photocatalyst 50 facing the flow path and the UV light source 51 irradiating the photocatalyst 50 with light including ultraviolet rays are provided as the air cleaning means 5 as in the first embodiment. As a matter of course, instead of this or in addition to this, the air cleaning means 5A for generating ions or radical active species by discharge of a high voltage to be applied to electrodes may be provided as in the second embodiment.

In this embodiment, an aromatic substance or a deodorant 53 is provided as an air cleaning means at an appropriate position facing the flow paths for the forced air flows a. The temperature increases up to around 30 to 40° C. in the flow paths including the light source support base 20 and the heat sink member 21 in particular, which allows the aromatic substance or deodorant to exert its action efficiently. The aromatic substance or deodorant 53 is detachably attached to the base end-side surface of the light source support base 20. By removing attachment screws not illustrated connecting the first case 11 and the second case 12 to separate the first case 11 and the second case 12 from each other, the inside aromatic substance or deodorant 53 can be replaced. This separable case facilitates replacement and maintenance of the UV light source 51, the fan 4, and the power supply circuit part 6.

In this embodiment, the power supply circuit part 6 is not formed by providing the circuit substrate 61 within the annular hollow resin case 60 unlike in the first and second embodiments, but is provided directly between the fan 4 and the air inlets/outlets 3B in the second case 12 such that the forced air flows a pass through a gap t between the circuit substrate 61 and the second case 12, and the circuit substrate 61 is cooled directly by the forced air flows a in an efficient manner.

In this embodiment, the lens body 14 is detachably attached by attachment screws 14a. Therefore, if the lens body 14 or the inner illumination light source 2 is broken, the device can be continuously used by replacing only the lens body 14 or the illumination light source 2, without having to replace the entire device.

Figure 5:
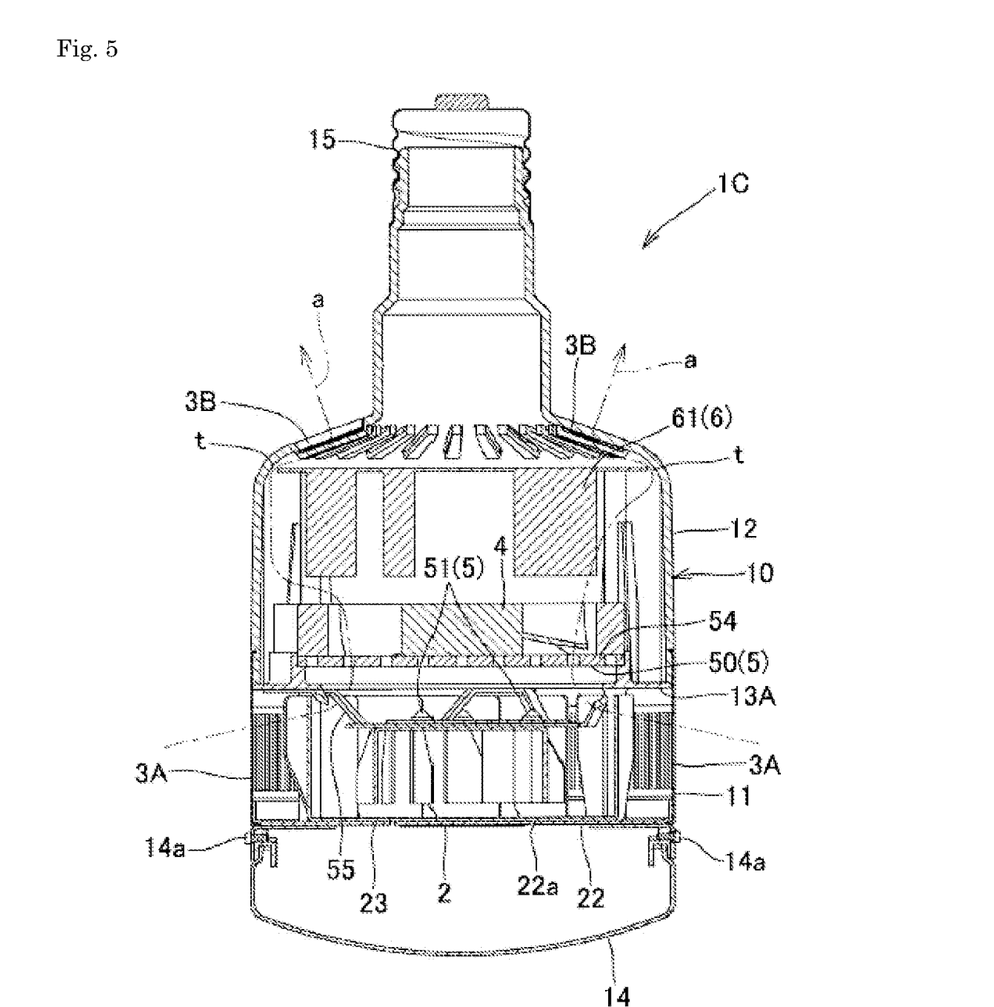
FIG. 5 is an illustrative cross-sectional view of an air cleaning device according to a fourth embodiment of the present invention.

Next, a fourth embodiment will be described with reference to FIG. 5.

In an air cleaning device 1C of this embodiment, a filter member 54 is provided in the middle of the flow paths for the forced air flows. The filter member 54 supports the photocatalyst 50 and is irradiated with ultraviolet rays from the UV light source 51. The filter member 54 may be made from any material capable of supporting a photocatalyst, and may be any of various filter members of ceramic, metal such as aluminum, synthetic resin, or paper.

In this example, a disc-shaped hollow support plate 13A is provided at a position close to the base end side beyond the support plate 23 of the illumination light source 2, specifically, at a position of the boundary between the first case 11 and the second case 12, and the filter member 54 is fixed to the support plate 13A. In addition, a fixing member 55 made from a highly thermal-conductive member of aluminum or the like is extended from the support plate 13A toward the leading end side and provided at an intermediate position between the support plate 13A and the support plate 23 to fix the UV light source 51 irradiating the filter member 54 at the base end side with ultraviolet rays.

When the UV light source 51 is fixed to the base end-side surface of the support plate 13/13A supporting the illumination light source as in the first and third embodiments, ultraviolet rays from the UV light source 51 are likely to leak to the outside from the air inlets/outlets 3A. The ultraviolet rays have a negative impact on the human body and it is thus preferred to provide the UV light source 51 at the intermediate position between the support plate 13A and the support plate 23 as in the fourth embodiment to reduce leakage of ultraviolet rays to the outside from the air inlets/outlets 3A in terms of safety.

The fan 4 is closely fixed by the support plate 13A to the base end side of the filter member 54. Other components and modifications, and the direction of the forced air flows a in the fourth embodiment are basically the same as those in the third embodiment. Accordingly, the same components are given the same reference signs and descriptions thereof are omitted.

Figure 6:
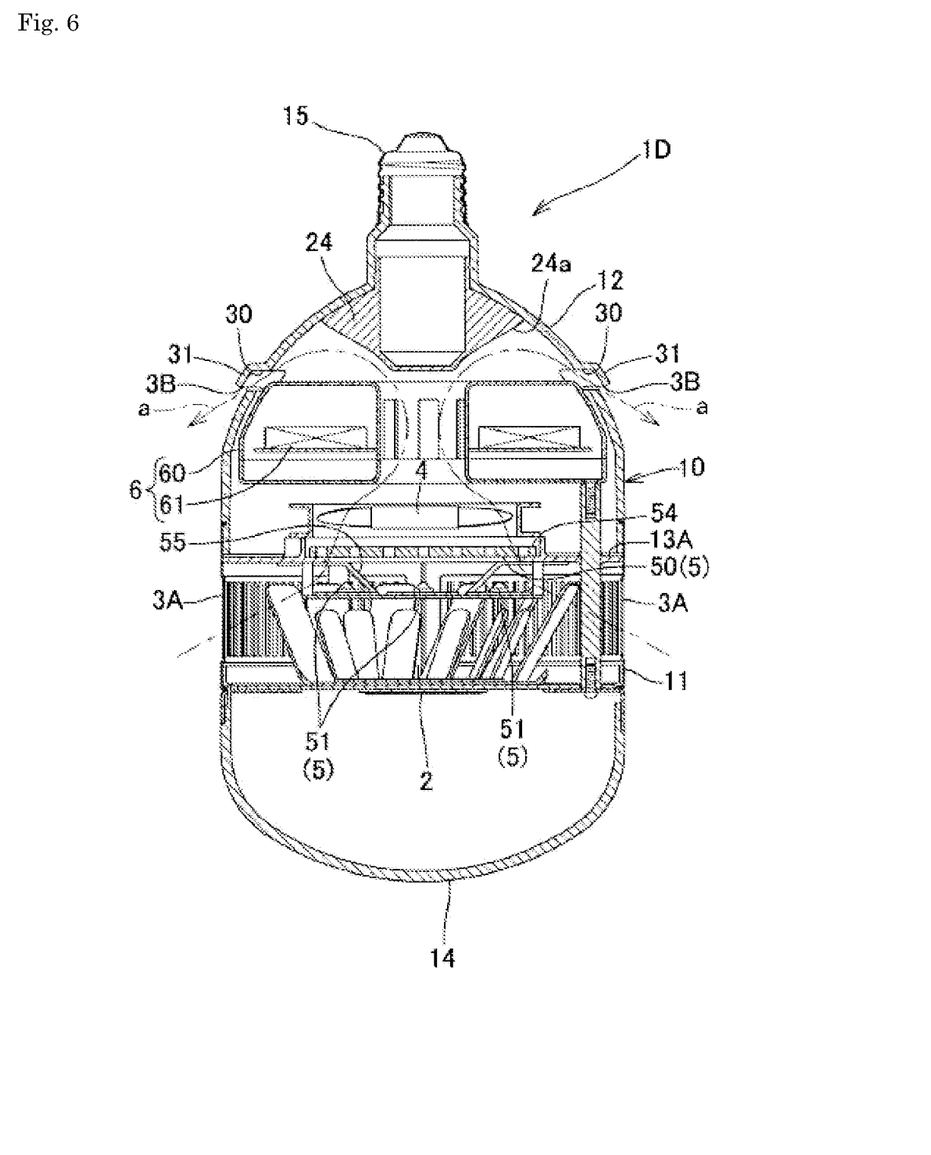
FIG. 6 is an illustrative cross-sectional view of an air cleaning device according to a fifth embodiment of the present invention.

Next, a fifth embodiment will be described with reference to FIG. 6.

In an air cleaning device 1D of this embodiment, an guide plates 31 bent in an L-shape are protruded outward from the base end-side edges of openings 30 in the second case 12 to allow the air inlets/outlets 3B to serve as outlet ports to release the forced air flows a toward the leading end side. Accordingly, it is possible to allow efficient supply of air cleaned by the air cleaning means 5 and released from the air inlets/outlets 3B toward the direction of irradiation by the illumination light source 2, that is, the leading end side.

In this example, an air convection member 24 with an air guide surface 24a gently inclined is provided at an appropriate position at the base end side of the annular hollow resin case 60 in the second case 12 to guide efficiently the forced air flows a having passed through the center of the resin case 60 for the power supply circuit part 6 to the air inlets/outlets 3B. The basic configuration of the device in this example is the same as that in the first embodiment, and the configuration of the air cleaning means 5, that is, the provision of the filter member 54 and the positional relation between the fan 4 and the UV light source 51 in this example are the same as those in the fourth embodiment. The same components as those in the foregoing embodiments are given the same reference signs as those in the foregoing embodiments and descriptions thereof are omitted.

Figure 7:
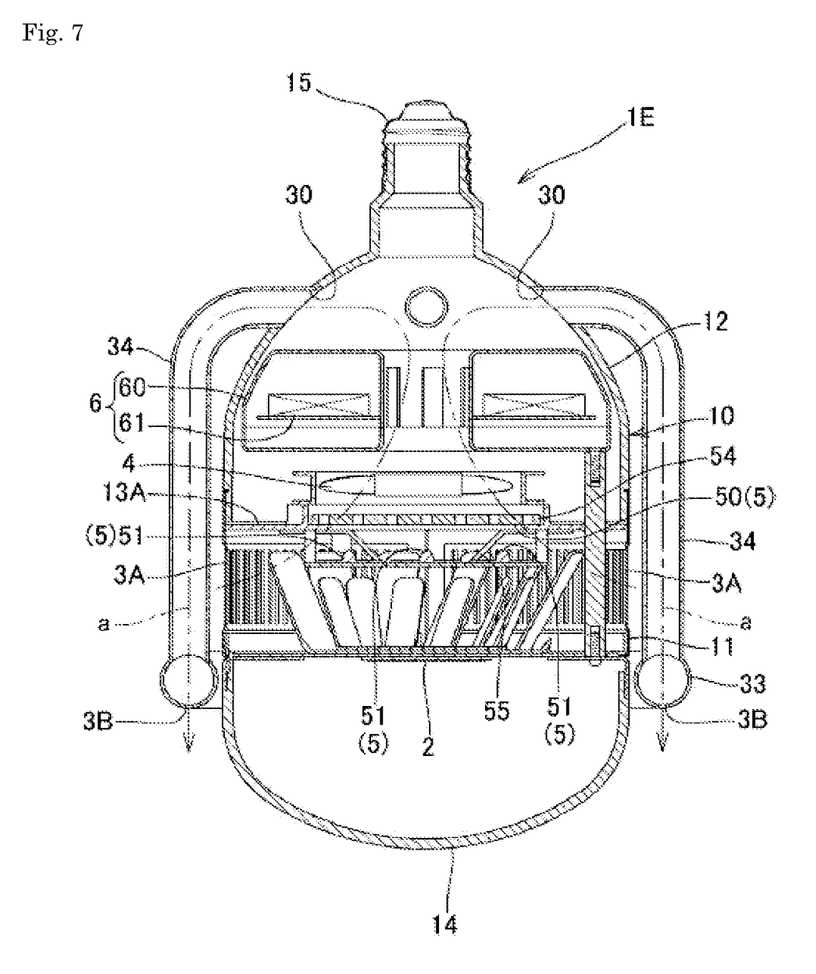
FIG. 7 is an illustrative cross-sectional view of an air cleaning device according to a sixth embodiment of the present invention.

Next, a sixth embodiment will be described with reference to FIG. 7.

An air cleaning device 1E in this embodiment includes, instead of the guide plates 31 constituting the air inlets/outlets 3B, guide pipes 32 each made from a highly thermal-conductive member of aluminum or the like. The guide plates 32 are protruded outward in communication with the openings 30 of the second case 12, bent in almost an L-shape along the side surfaces of the housing 10, extended toward the leading end side at least beyond the opening positions of the air inlets/outlets 3A, and opened toward the outside. In this example, annular pipes 33 with a large number of openings as the air inlets/outlets 3B in the leading end surfaces are provided at positions close to the leading end side beyond the openings of the air inlets/outlets 3A and at the base end side of the lens body 14 not cutting off illumination light. A plurality of connection pipes 34 bent in an almost L-shape and extended from the openings 30 of the second case 12 is communicated with and connected to the annular pipes 33.

The air from the air inlets/outlets 3B in the annular pipes 33 is evenly released like a shower toward the leading end side. In this example, the guide pipes 32 are composed of the annular pipes 33 and the connection pipes 34 but may be configured in any other manner. The annular pipes 33 are supported by the plurality of connection pipes 34, four in this example, connected at equal spaces in a circumferential direction.

In the fifth embodiment, part of the air released from the air inlets/outlets 3B toward the leading end side is taken again into the air inlets/outlets 3A. According to the configuration of this embodiment, the guide pipes 32 allows the air inlets/outlets 3B to be positioned close to the leading end side beyond the air inlets/outlets 3A to release and supply the clean air toward the leading end side in a more reliable and efficient manner. The guide pipes 32 serve as heat sinks.

No air convection member is provided in the second case 12. However, an air convection member may be provided at an appropriate position at the base end side of the resin case 60 as in the fifth embodiment. Other components and modifications of this embodiment are basically the same as those in the fifth embodiment, and the same components are given the same reference signs and descriptions thereof are omitted.

Figure 8:
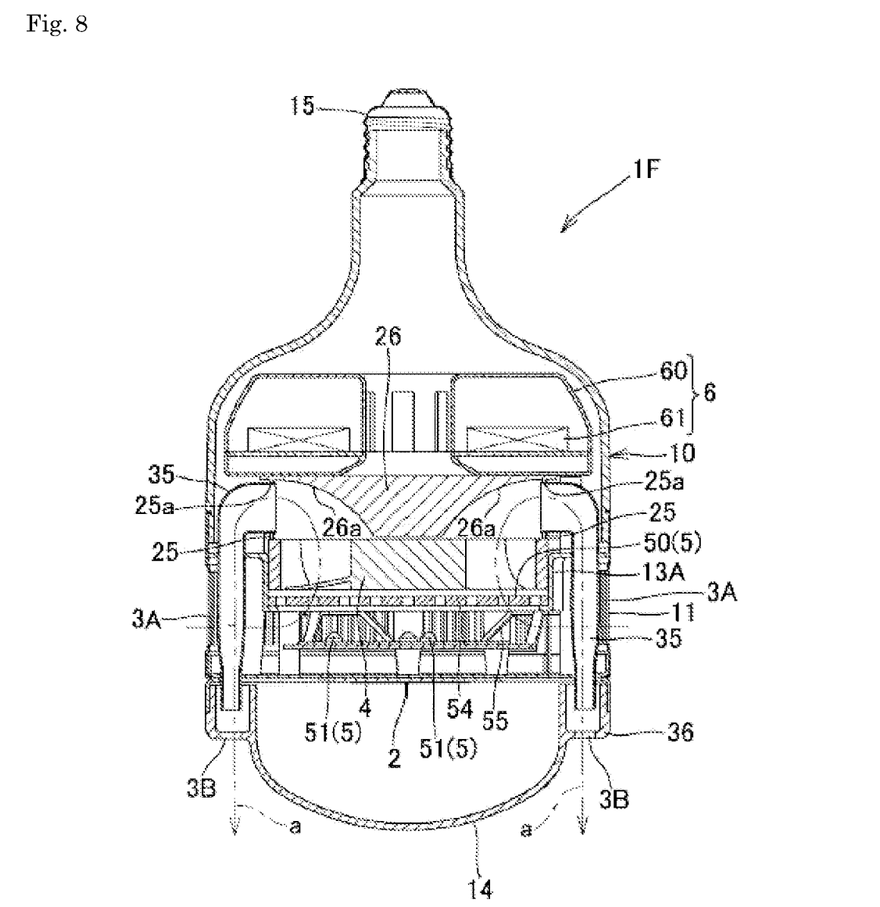
FIG. 8 is an illustrative cross-sectional view of an air cleaning device according to a seventh embodiment of the present invention.

Next, a seventh embodiment will be described with reference to FIG. 8.

Under the concept of an air cleaning device 1F in this embodiment, the guide pipes 32 in the sixth embodiment are provided within the housing 10. In the sixth embodiment, the openings 30 are provided at the positions close to the base end side beyond the resin case 60 for the power supply circuit part 6 in the housing 10, and the guide pipes 32 are protruded toward the outside from the openings 30. In this embodiment, peripheral wall parts 25 are formed to form flow paths between the resin case 60 and the fan 4 in the housing 10, and a plurality of openings 25a is formed in the peripheral wall parts 25, and inner pipes 35 each made from a highly thermal-conductive member of aluminum or the like are provided. The inner pipes 35 are connected at the base end side to the openings 25a, bent in almost an L-shape, extended toward the leading end side in the housing 10, and communicated with the air inlets/outlets 3B opened outward at the positions close to the leading end side beyond the air inlets/outlets 3A.

The inner pipes 35 allow supply of the clean air toward the leading end side in an efficient and reliable manner as in the sixth embodiment without deterioration in the appearance of the device. The inner pipes 35 communicate with circular air retention parts 36 integrally formed with the lens body 14 at the base end side of the lens body 14. A large number of openings as the air inlets/outlets 3B is formed in the leading end surfaces of the air retention part 36. The air released from the air inlets/outlets 3B of the air retention part 36 is evenly released like a shower toward the leading end side. In this example, an air convection member 26 with air guide surfaces 26a gently inclined is provided in the flow paths in the inner side of the peripheral wall parts 25 to guide efficiently the forced air flows a having passed through the fan 4 to the openings 25a in the peripheral wall parts 25.

Similar peripheral wall parts may be provided at the base end side of the resin case 60 for the power supply circuit part 6 and similar internal pipes may be disposed from the openings in the peripheral wall parts through the gap between the resin case 60 and the second case 12. Other components and modifications in this embodiment are basically the same as those in the sixth embodiment, and the same components are given the same reference signs and descriptions thereof are omitted.

Figure 9:
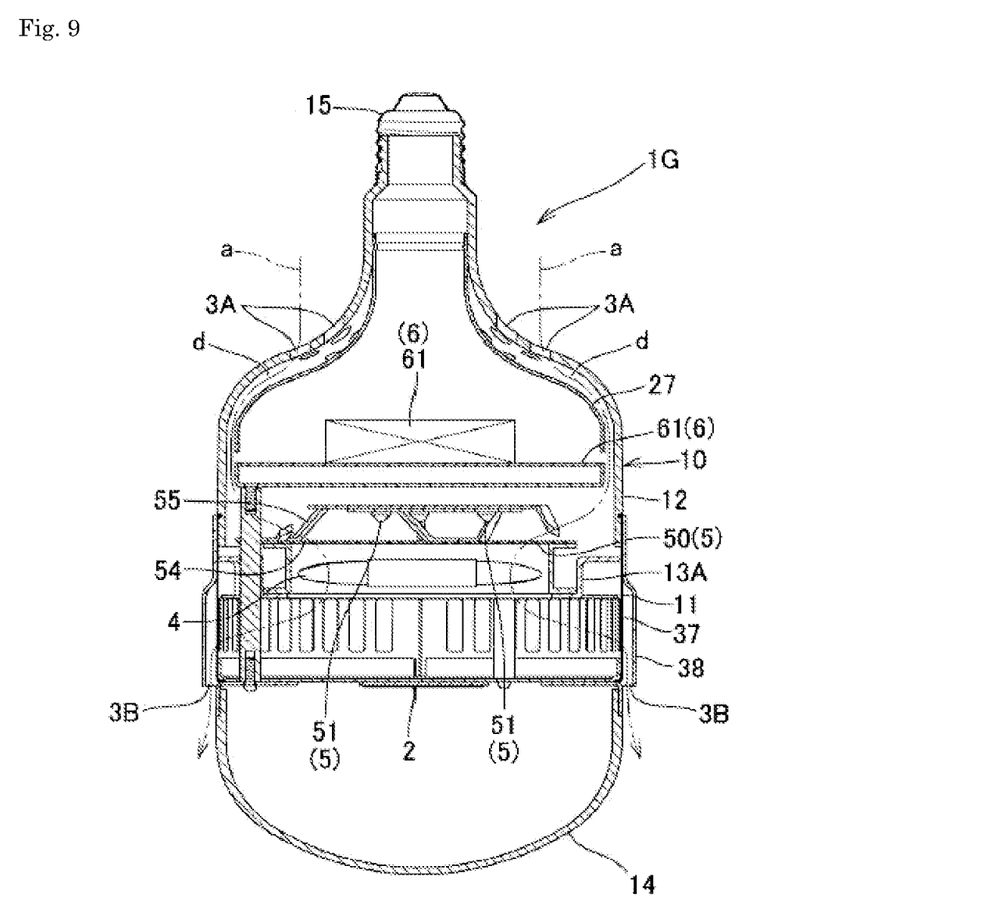
FIG. 9 is an illustrative cross-sectional view of an air cleaning device according to an eighth embodiment of the present invention.

Next, an eighth embodiment will be described with reference to FIG. 9.

In an air cleaning device 1G of this embodiment, the fan 4, the filter member 54, and the UV light source 51 are arranged in reverse at the leading end side and the base end side from the fourth to seventh embodiments, such that the forced air flows a are passed from the base end side to the leading end side. Specifically, the disc-shaped hollow support plate 13A is provided at a position close to the base end side beyond the support plate 23 of the illumination light source 2, specifically, at a position of the boundary between the first case 11 and the second case 12. The fan 4 is fixed to the support plate 13A. The filter member 54 is fixed to the base end side of the fan 4. In addition, the fixing member 55 is provided at the base end side to fix the UV light source 51 irradiating the filter member 54 with ultraviolet rays from the base end side.

As in the fourth to seventh embodiments, the UV light source 51 is provided at the upstream side of the air flow, not the downstream side, beyond the fan 4 such that the air pushed out of the fan 4 reaches efficiently the air inlets/outlets 3B without interference by the UV light source or the like. In this example, a guide plate 38 made from a highly thermal-conductive member of aluminum or the like is protruded. The guide plate 38 is bent in an L-shape to cover openings 37 in the first case 11 as release ports of the forced air flows a at the leading end side, such that the forced air flows a can be released toward the leading end side. The openings at the leading end side of the gap between the guide plate 38 and the first case 11 serve as the air inlets/outlets 3B.

In this example, an air convection member 27 of almost the same shape as the second case 12 is provided inside the second case 12 to guide the forced air flows a sucked through the air inlets/outlets 3A toward the leading end side through the gap d from the second case 12. In addition, the power supply circuit part 6 composed of the circuit substrate 61 is disposed inside the air convection member 27 such that the forced air flows a do not hit directly the power supply circuit part 6. Disposing the circuit substrate 61 in the middle of the flow paths for the forced air flows a causes accumulation of dust and the like, but the air convection member 27 prevents this problem.

Other components and modifications in this embodiment are basically the same as those in the third to seventh embodiments, and the same components are given the same reference signs and descriptions thereof are omitted.

Figure 10:
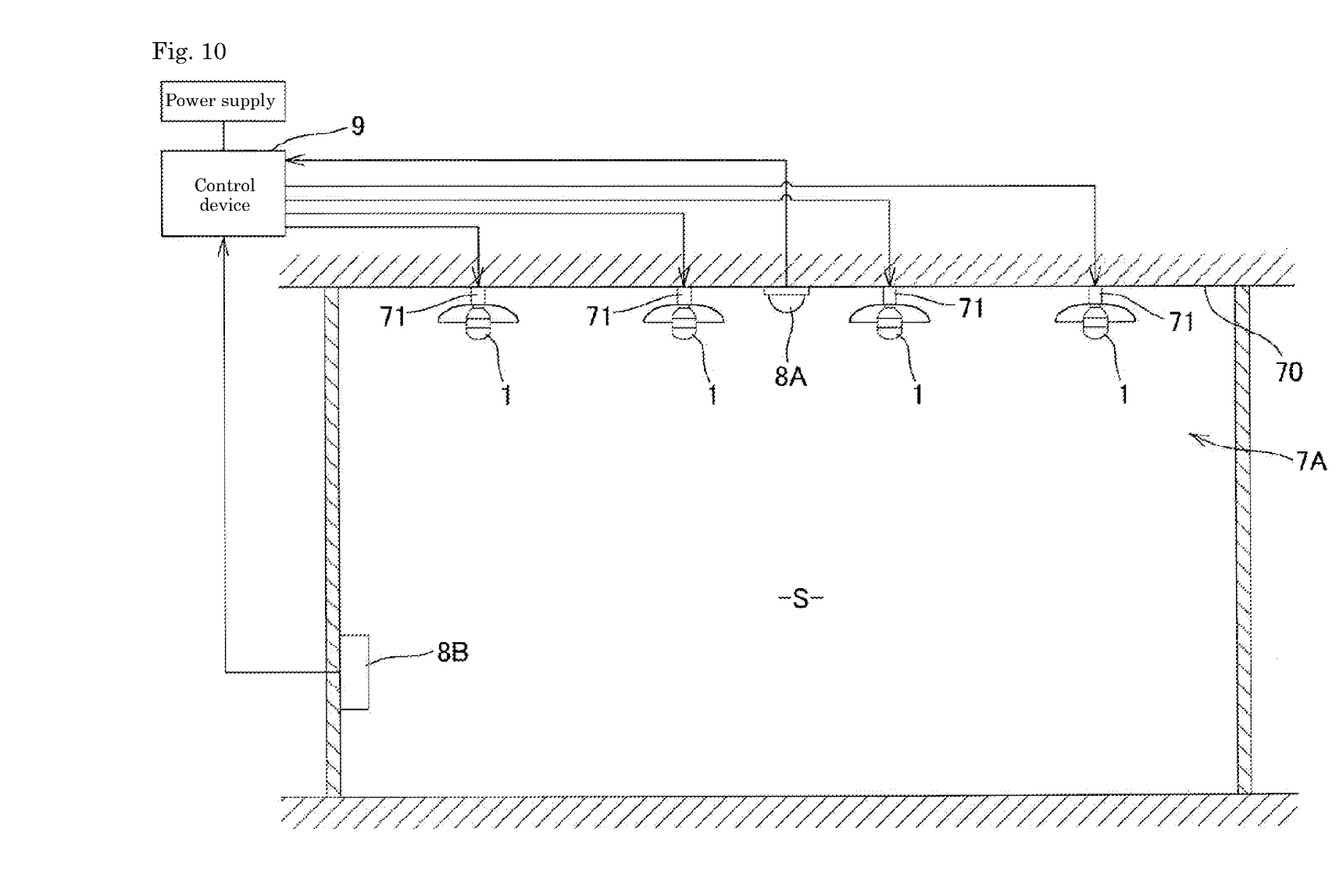
FIG. 10 is an illustrative view of an air cleaning system according to a ninth embodiment of the present invention.

Next, a ninth embodiment will be described with reference to FIG. 10.

According to this embodiment, the foregoing air cleaning system 7 is provided with a human detection sensor 8A, an odor sensor 8B, and a control device 9 controlling the operations of the air cleaning devices 1. The control device 9 includes a CPU, a power supply circuit connected to the CPU, a drive circuit for the fan 4 in the air cleaning device 1, a drive circuit for the illumination light source 2 in the air cleaning device 1, a drive circuit for the UV light source 51 in the air cleaning device 1. The CPU in the control device 9 is connected to the human detection sensor 8A, the odor sensor 8B, and an operation panel not illustrated, and the like.

The CPU in the control device 9 serves as processing parts that perform processes according to programs stored in advance in a storage part. In this example, one of the processing parts adjusts the amounts of wind from the fans 4 and the outputs from the UV light sources 51 according to the detected odor level from the odor sensor. In addition, another processing part adjusts the outputs from the illumination light sources 2 according to the signal from the human detection sensor 8A. When no signal is sent from the human detection sensor 8A, that is, when no person exists there, it is preferred that the illumination light sources 2 are turned off and the UV light sources 51 and the fans 4 alone are operated. In this case, it is preferred that the outputs from the fans 4 are reduced and the outputs from the UV light sources 51 are increased.

In this example, the human detection sensor 8A may be any publicly-known moving object detection sensor such as an infrared sensor, an ultrasonic sensor, or a laser sensor. The human detection sensor 8A and the odor sensor 8B are provided on a ceiling surface or wall surface constituting the space S outside the air cleaning devices 1. Alternatively, the human detection sensor 8A and the odor sensor 8B may be provided in the air cleaning device 1. The air cleaning devices 1 may be any of the devices in the foregoing embodiments. Other components and modifications of the air cleaning system are basically the same as those described above in relation to the first embodiment, and the same components are given the same reference signs and descriptions thereof are omitted.

Figure 11:
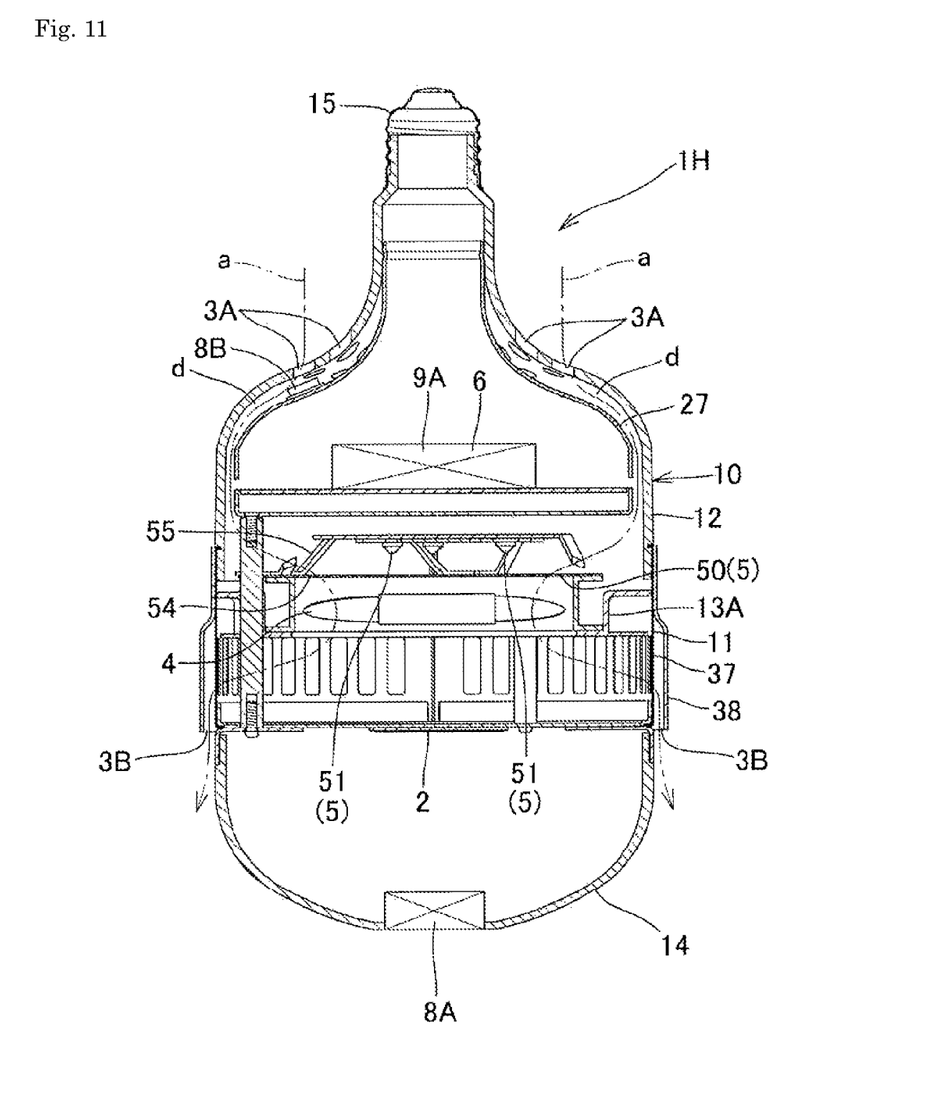
FIG. 11 is an illustrative cross-sectional view of an air cleaning device according to a tenth embodiment of the present invention.

Next, a tenth embodiment will be described with reference to FIG. 11.

An air cleaning device 1H in this embodiment includes therein the human detection sensor 8A, the odor sensor 8B, the power supply circuit part 6, and a control device 9A (controller) connected to the human detection sensor 8A and the odor sensor 8B. The control device 9A includes a CPU, the power supply circuit part 6, and a drive circuit for the fan 4, a drive circuit for the illumination light source 2, and a drive circuit for the UV light source 51 similar to the control device 9 in the ninth embodiment. The CPU is connected to the human detection sensor 8A, the odor sensor 8B, an operation panel provided in the housing but not illustrated, and the like, similar to the control device 9 in the ninth embodiment.

The CPU of the control device 9A serves as processing parts that perform processes according to programs stored in advance in a storage part. In this example, one of the processing parts adjusts the amount of wind from the fan 4 and the output from the UV light source 51 according to the detected odor level from the odor sensor. In addition, another processing part adjusts the output from the illumination light source 2 according to the signal from the human detection sensor 8A. Other operations of the control device in this embodiment are the same as those in the ninth embodiment. Other operations of the control device are the same as those in the ninth embodiment. Other components of the air cleaning device are the same as those described above in relation to the foregoing embodiments, and the same components are given the same reference signs and descriptions thereof are omitted.

The embodiments of the present invention have been described above so far. However, the present invention is not limited to these embodiments and can be carried out in various other manners without deviating from the gist of the present invention.

REFERENCE SIGNS LIST

1, 1A to 1H Air cleaning device
2 Illumination light source
3A and 3B Air inlets/outlets
4 Fan
5 and 5A Air cleaning means
6 Power supply circuit part
7 Air cleaning system
8A Human detection sensor
8B Odor sensor
9 and 9A Control device
10 Housing
11 First case
12 Second case
13 Support plate
13A Support plate
14 Lens body
14a Attachment screw
15 Base 20 Light source support base
20a Inner surface
21 Heat sink member
22 Base plate
22a Opening
23 Support plate
24 Air convection member
24a Air guide surface
25 Peripheral wall part
25a Opening
26 Air convection member
26a Air guide surface
27 Air convection member
30 Opening
31 Guide plate
32 Guide pipe
33 Annular pipe
34 Connection pipe
35 Inner pipe
36 Air retention part
37 Opening
38 Guide plate
50 Photocatalyst
51 Light source
52 Electrode
53 Deodorant
54 Filter member
55 Fixing member
60 Resin case
61 Circuit substrate
70 Ceiling
71 Socket
a Forced air flow
d Gap
t Gap
S Space

The invention claimed is:

1. An air cleaning device, wherein
air inlets/outlets are provided in a housing to which an illumination light source is attached,
a fan is provided in the housing to generate a forced air flow inside and outside the housing through the air inlets/outlets and discharge heat from the illumination light source by the forced air flow to the outside of the housing, and
an air cleaning means is provided in the middle of a flow path for the forced air flow within the housing,
wherein a light source support base is provided, the light source support base being made from a highly thermal-conductive member with an outer surface to which the illumination light source is fixed, and an inner surface of the light source support base opposite to the illumination light source constitutes an inner wall surface of the flow path,
wherein a heat sink member made from a highly thermal-conductive member is protruded from the inner surface of the light source support base, and
the heat from the light source support base is discharged via the heat sink member to the forced air flow passing through the flow path.

2. The air cleaning device according to claim 1, wherein the illumination light source is composed of an illumination LED.

3. The air cleaning device according to claim 1, wherein the air cleaning means is a photocatalyst facing the flow path and an UV light source irradiating the photocatalyst with light including ultraviolet rays.

4. The air cleaning device according to claim 3, wherein the UV light source is fixed to the inner surface of the light source support base or the heat sink member.

5. The air cleaning device according to claim 3, wherein the UV light source is composed of an ultraviolet LED.

6. The air cleaning device according to claim 1, wherein the air cleaning means is a means for generating ions or radical active species by discharge of a high voltage to be applied to electrodes.

7. The air cleaning device according to claim 1, wherein the air cleaning device is a light bulb type with a base to which power is supplied from the outside.

8. An air cleaning method comprising:
disposing one or more air cleaning devices according to claim 1 on an inner surface of a space divided from others and intended as a humans' or animals' activity space or as a storage space for objects;
illuminating the inner space by the air cleaning device;
taking into the housing the air from the inner space as the forced air flow; and
cleaning the air by the air cleaning means in the middle of the flow path and emitting the same to the outside of the housing, thereby to clean the air in the inner space.

9. The air cleaning method according to claim 8, wherein
the air cleaning device is a light bulb type with a base to which power is supplied from the outside,
the air cleaning device is detachably attached through the base to the inner surface of the storage space,
a socket is provided to supply power to the attached air cleaning device, and
the illumination light source, the fan, and the air cleaning means in the air cleaning device are operated by the power supply.

10. An air cleaning system, wherein
one or more air cleaning devices according to claim 1 are disposed on an inner surface of a space divided from others and intended as a humans' or animals' activity space or as a storage space for objects,
the inner space is illuminated by the air cleaning device;
the air in the inner space is taken into the housing as the forced air flow; and
the air is cleaned by the air cleaning means in the middle of the flow path and is emitted to the outside of the housing, thereby to clean the air in the inner space.

11. The air cleaning system according to claim 10, wherein
the air cleaning device is a light bulb type with a base to which power is supplied from the outside,
the air cleaning device is detachably attached through the base to the inner surface of the storage space,
a socket is provided to supply power to the attached air cleaning device, and
the illumination light source, the fan, and the air cleaning means in the air cleaning device are operated by the power supply.

* * * * *